United States Patent
Shalyt et al.

(10) Patent No.: US 7,932,094 B2
(45) Date of Patent: Apr. 26, 2011

(54) METHOD AND APPARATUS FOR DETERMINING THE STABILITY OF AN ELECTROLESS PLATING BATH

(75) Inventors: Eugene Shalyt, Washington Township, NJ (US); Semyon Aleynik, Tenafly, NJ (US); Peter Bratin, Flushing, NY (US)

(73) Assignee: ECI Technology, Inc., Totowa, NJ (US)

( * ) Notice: Subject to any disclaimer, the term of this patent is extended or adjusted under 35 U.S.C. 154(b) by 131 days.

(21) Appl. No.: 12/228,008

(22) Filed: Aug. 7, 2008

(65) Prior Publication Data

US 2010/0035356 A1    Feb. 11, 2010

(51) Int. Cl.
*G01N 31/16* (2006.01)
*G01N 31/00* (2006.01)

(52) U.S. Cl. ............ 436/163; 422/75; 422/68.1; 422/50
(58) Field of Classification Search ............... 436/163; 422/75, 68.1, 50; 356/229, 213, 432, 433
See application file for complete search history.

(56) References Cited

U.S. PATENT DOCUMENTS

| | | | |
|---|---|---|---|
| 4,762,601 A * | 8/1988 | Krulik et al. | 427/345 |
| 4,774,101 A * | 9/1988 | Harris et al. | 427/8 |
| 4,904,506 A * | 2/1990 | Burnett et al. | 427/443.1 |
| 4,950,610 A * | 8/1990 | Tittle | 436/163 |
| 2008/0241401 A1 * | 10/2008 | Choi et al. | 427/304 |

OTHER PUBLICATIONS

Yin X., et al, Modeling the stability of electroless plating bath-diffusion of nickel colloidal particles from the plating frontier, Journal of Colloid and Interfaces Science, 2003, 262, 89-96.*

* cited by examiner

*Primary Examiner* — Walter D Griffin
*Assistant Examiner* — Christine T Mui
(74) *Attorney, Agent, or Firm* — D. Morgan Tench

(57) ABSTRACT

The stability of an electroless plating bath for depositing a metal (e.g., nickel) is determined by titrating a sample of the plating bath with a titrant comprising ions of a catalytic metal (e.g., palladium) and detecting hydrogen released at the titration endpoint. The quantity of titrant required to attain the endpoint provides a measure of the stability of the electroless plating bath.

12 Claims, 2 Drawing Sheets

METHOD AND APPARATUS FOR DETERMINING THE STABILITY OF AN ELECTROLESS PLATING BATH

BACKGROUND OF THE INVENTION

1. Field of the Invention

This invention is concerned with analysis of electroless plating baths and in particular with determining the stability of such baths against decomposition.

2. Description of the Related Art

Plating baths are widely used by the electronics industry to deposit a variety of metals (copper, nickel, cobalt and gold, for example) on various parts, including circuit boards, semiconductor chips, and device packages. Both electroplating baths and electroless plating baths are employed. For electroplating, the part and a counter electrode are brought into contact with the electroplating bath containing ions of an electrodepositable metal, and the metal is electrodeposited by applying a negative potential to the part relative to the counter electrode. For electroless plating, the bath also contains a reducing agent which, in the presence of a catalyst, chemically reduces the metal ions to form a deposit of the metal. Since the deposited metal itself can serve as the catalyst, the electroless deposition, once initiated, proceeds without the need for an externally applied potential. In immersion plating, substrate oxidation provides the electrons needed to electrolessly deposit a layer of a more noble metal. The immersion plating process is self-limiting, i.e., ceases when the substrate is fully covered with the deposited metal.

Among electroless processes, those for depositing nickel and cobalt are particularly important to the electronics industry, and other industries as well. For example, electroless nickel with an immersion gold surface layer (ENIG) is widely used to provide an oxidation-resistant and solderable/bondable finish on copper circuitry and surface pads on circuit boards, and on aluminum pads on semiconductor chips. As another example, electroless cobalt and nickel processes are used to provide electrically-conductive and conformal barrier and capping layers for copper circuitry on semiconductor chips as part of the well-known "Damascene" process. Electroless cobalt and nickel baths used to deposit Damascene barrier and capping layers typically also contain a refractory metal (e.g., tungsten, molybdenum or rhenium), which co-deposits with the cobalt or nickel and increases the maximum temperature at which effective barrier properties are retained.

For electroless cobalt and nickel baths, hypophosphite ($H_2PO_2^-$) is typically used as the reducing agent, which introduces phosphorus into the deposit. The codeposited phosphorus reduces the deposit grain size and crystallinity (compared to electrodeposits), which tends to improve the barrier properties and oxidation resistance of the deposit. Alternative reducing agents include the boranes, dimethylamineborane (DMAB), for example. Use of a borane reducing agent introduces boron into the deposit.

A typical bath for electroless deposition of Damascene barrier layers comprises 0.1 M cobalt chloride or sulfate, 0.2 M sodium hypophosphite, 0.03 M sodium tungstate, 0.5 M sodium citrate, 0.5 M boric acid, and a small amount of a surfactant. Such Co(W, P) baths typically operate at about pH 9 and a temperature of 85°-95° C., and may also contain organic additives.

For electroless deposition of cobalt and nickel on dielectric materials, such as silicon oxide, or on metals that are not sufficiently catalytic for the electroless process, such as copper, a seed layer of a catalytic metal is generally employed. Catalytic palladium is typically deposited on silicon dioxide by immersion of the part in an acidic activator solution containing palladium chloride and fluoride ion. The fluoride ion tends to cause dissolution of surface oxides on the substrate so that a displacement layer of palladium is formed. Alternatively, a seed layer of the electrolessly deposited metal, cobalt or nickel, may be applied by sputtering. For electroless deposition of cobalt and nickel on aluminum, the aluminum substrate is first zincated in an alice solution, which provides a zinc surface layer that dissolves in the electroless bath prior to deposition of cobalt or nickel.

Recently, direct deposition of Co(W, P) capping layers on Damascene copper circuits from a bath employing two reducing agents was reported [T. Itabashi, N. Nakano and H. Akahoshi, Proc. IITC 2002, p. 285-287]. In this case, electroless deposition is initiated by the more active reducing agent (DMAB), which is present at a relatively low concentration. As the DMAB reducing agent becomes depleted at the part surface, electroless deposition is sustained by the less active reducing agent (hypophosphite), which provides better deposit properties.

Electroless copper baths are also widely used by the electronics industry to provide conductive seed layers on poorly conductive substrates. Electroless copper baths typically contain copper sulfate, a complexing agent (e.g., EDTA), a reducing agent (e.g., formaldehyde or glyoxilic acid), a stabilizer (e.g., 2,2-dipyridyl), and hydroxide ion (added as sodium hydroxide or tetramethylammonium hydroxide).

Close control of the concentrations of the constituents of electroless plating baths is necessary to provide acceptable deposit properties. Some constituents can be detected by standard analytical techniques whereas specialized methods are needed to measure the concentrations of other constituents. A method for measuring the concentration of reducing agents in electroless plating baths, based on metal electrodeposition rate measurements, is described in U.S. Pat. No. 6,709,561 to Pavlov et al. (issued Mar. 23, 2004)). A method for measuring the concentration of complexing agents in electroless plating baths, based on titration with a metal complexing ion (e.g., $La^{3+}$) and endpoint detection via a fluoride ion indicator, is described in a U.S. Pat. No. 6,890,758 to Shalyt et al. (issued May 10, 2005).

One important control parameter for electroless plating baths is the bath stability. A compromise is required in that the bath must provide both an acceptable metal deposition rate and resistance to spontaneous decomposition (in the absence of a catalyst). This compromise is inherent in the selection of the bath complexing agent (which tends to stabilize the metal ions in the bath) and the reducing agent (which tends to chemically reduce the metal ions). Generally, for a given bath formulation, bath stability is increased by addition of the complexing agent and is decreased by addition of the reducing agent.

However, other factors also affect the stability of electroless plating baths so that the bath stability typically cannot be predicted based on measurements of the concentrations of the bath complexing agent and reducing agent. In particular, plating baths are usually proprietary formulations that may include surfactants, organic additives (designed to improve the deposit properties) and/or other bath stabilizers, which may comprise additional inorganic complexing agents and/or organic species. The bath makeup and replenishment chemicals are typically provided as proprietary solutions that contain multiple species whose concentrations are not disclosed, making it difficult to determine the effects of individual species. Furthermore, bath breakdown products (especially of organic species) and bath contaminants (derived from substrate materials and/or drag-in, for example) may also affect the bath stability. It is generally impractical to predict the stability of an electroless plating bath by measuring the concentrations of each species involved, especially since the effects exerted may involve interference or synergy.

Consequently, a means of measuring the stability of electroless plating baths is needed. Such a means would enable the bath to be replaced as-needed rather than according to a schedule, reducing the costs and environmental impact of electroless plating processes. In addition, the close process control provided would enable the stability of the bath to be more closely matched to the requirements of the process to improve the deposit properties. For example, the bath stability might be reduced (by increasing the reducing agent concentration or decreasing the bath complexing agent concentration) to improve substrate coverage. Early detection of bath instabilities that affect the quality of the deposit would also reduce the costs and impact of scrap. A bath instability might result, for example, from a bath contaminant or a variation in a control parameter, such as bath temperature.

A recent publication [R. W. M. Kwok, K. C. M. Chan and M. W. Bayes, "Development of an Electroless Nickel Immersion Gold Process for PCB Final Finishes", Circuit World 30(3), 37-42 (2004)], which is hereby incorporated by reference, describes a method for measuring the stability of an ENIG electroless nickel plating bath "by titrating the bath solution with a palladium solution until nickel starts depositing on the apparatus wall". This publication introduces a stability index proportional to the amount of palladium titrant needed to produce a nickel deposit. The titration endpoint used for this prior art approach, which involves nickel deposition on a vessel wall, is difficult to detect precisely and renders the titration analysis method time-consuming and difficult to automate. In particular, nickel deposits tend to passivate and are typically removed by dissolution in strong acid solution.

An objective of the present invention is to provide a relatively precise method for measuring the stability of electroless plating baths that can be effected under computer control. Another objective of the invention is to provide an automated apparatus for practicing the method of the invention.

SUMMARY OF THE INVENTION

The invention provides a method and an apparatus for measuring the stability of an electroless plating bath for depositing a metal. The method involves titrating a sample of the electroless plating bath with a titrant solution comprising ions of a catalytic metal that catalyzes deposition of the deposited metal. The endpoint of the titration is indicated by evolution of hydrogen gas, which is a byproduct of the electroless metal deposition process. The evolved hydrogen gas is detected in the gas phase above the bath sample via a hydrogen detector. In this case, hydrogen is detected as a chemical species, not as physical bubbles in the bath sample. The analysis cell containing the bath sample may be open, shielded or closed with respect to the ambient atmosphere. The volumes of the analysis cell and the bath sample are preferably small so as to provide good sensitivity for detection of the onset of hydrogen evolution.

The invention provides a relatively precise method for measuring the stability of electroless plating baths that can be effected under computer control. In particular, hydrogen gas detection should provide a much sharper endpoint than the electroless metal deposition endpoint used in the prior art. In addition, the early endpoint detection provided by the invention enables early termination of the titration so as to minimize the quantity of metal that is electrolessly deposited on the cell walls and must be removed by cell cleaning. This is a particular issue for nickel and cobalt deposits, which tend to passivate and dissolve slowly in cleaning solutions. By minimizing the amount of metal deposited electrolessly on the cell walls during the titration, the invention reduces the cell cleaning time and minimizes the cost of the cleaning agent, typically an acid, and its disposal. The invention also provides an automated apparatus for measuring the stability of electroless plating baths, whereas prior art methods are not amenable to automation.

Further features and advantages of the invention will be apparent to those skilled in the art from the following detailed description, taken together with the accompanying drawings.

DETAILED DESCRIPTION OF THE INVENTION

Figure 1:
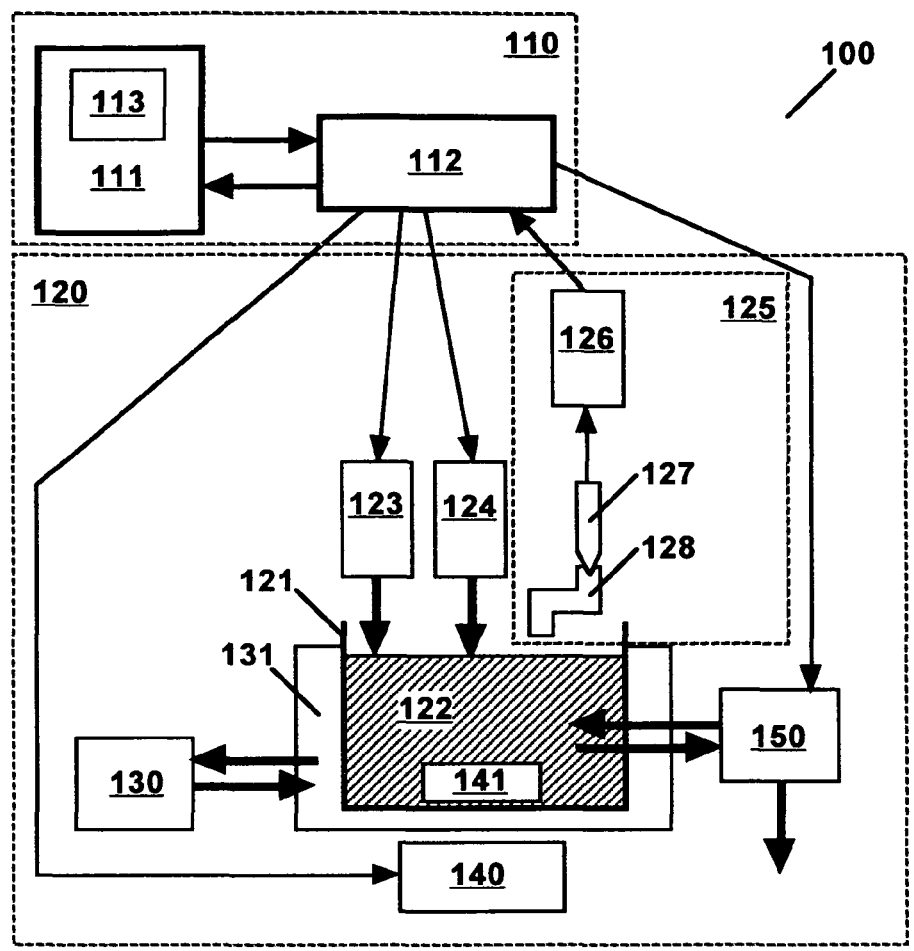
FIG. 1 is a schematic representation of a preferred apparatus of the invention.

Technical terms used in this document are generally known to those skilled in the art. The term "complexing agent" refers to complexation of the metal deposited from the electroless plating bath. The term "bath complexing agent" refers to the complexing agent present in the plating bath to stabilize the deposited metal ions so as to prevent precipitation of compounds of the deposited metal. The symbol "M" means molar concentration.

A "titrant solution" is a standard solution comprising a known concentration of a reagent called a "titrant" that chemically reacts with a "reactant" or "unknown species" whose concentration in a sample solution is to be determined. A "titration" is an analytical procedure involving repeated standard addition of a known volume of a titrant solution to a sample solution, coupled with monitoring the concentration of an indicator species, which participates in the reaction between the titrant and the reactant, or is indirectly affected by this reaction. The "equivalence point" is the point in a titration at which the reaction between the titrant and the reactant is complete, corresponding to a stoichiometric balance between the number of moles of the titrant and the number of moles of reactant with respect to formation of a compound or complex. The "titration endpoint" corresponds to a rapid change in the concentration of the indicator species as additional titrant is added to the sample solution after the equivalence point has been reached.

A "titration curve" is a plot of the concentration of a titration indicator species in a sample solution, or a parameter proportional to this concentration, as a function of the volume of titrant solution added to the sample solution. The proportional relationship between the parameter and the concentration may be linear or nonlinear, logarithmic or exponential, for example. The endpoint for the titration is typically determined from a curve feature corresponding to a rapid change in the concentration of the indicator species. The titration endpoint may be determined using any suitable titration curve feature, including an inflection point, a knee or a predetermined parameter value, for example. Detection of the titration endpoint may be facilitated by differentiating the titration curve, which converts an inflection point into a peak. Titration data are typically handled as titration curves or plots but such data may be tabulated and used directly, especially by a computer, and the term "titration curve" includes tabulated data.

The invention provides a method and an apparatus for measuring the stability of an electroless plating bath for depositing a deposited metal. The invention is useful for analysis of electroless plating baths for depositing nickel, cobalt, copper, tungsten, molybdenum, rhenium, and combinations thereof. Baths for depositing cobalt or nickel typically employ hypophosphite and/or borane reducing agents. The invention is particularly useful for analysis of electroless nickel baths used to provide solderable/bondable finishes for copper and aluminum integrated circuits, electroless cobalt and nickel baths used to provide barrier and capping layers for copper circuitry on semiconductor chips in the Damascene process, and electroless copper baths of the types used generally by the electronics industry.

The method of the invention comprises the steps of: (1) placing a predetermined volume of a sample of the electroless plating bath in an analysis cell; (2) stirring the sample; (3) maintaining the sample at a predetermined temperature; (4) providing a titrant solution comprising a predetermined concentration of ions of a catalytic metal that catalyzes deposition of the deposited metal; (5) performing a titration by repeatedly adding an aliquot of a known volume of the titrant solution to the sample and monitoring the concentration of hydrogen in the gas phase above the sample; (6) determining a titration endpoint corresponding to a substantial increase in the concentration of hydrogen in the gas phase above the sample; and (7) calculating the total quantity of the catalytic metal added to the sample at the titration endpoint, which provides a measure of the stability of the electroless plating bath. The sample is preferably stirred continuously during the titration but may alternatively be stirred periodically or intermittently.

The titrant solution preferably contains from 10 to 1000 ppm palladium chloride ($PdCl_2$) and from 10 to 200 g/L hydrochloric acid, which is added to prevent hydrolysis of the palladium salt. Other palladium salts and other catalytic metal titrants could be used. The titrant solution may comprise a palladium compound selected from the group consisting of chloride, sulfate, acetate and combination thereof, for example.

The apparatus of the invention enables automated application of the method of the invention. The apparatus comprises a titration analysis system and a computing system, which comprise the elements of the invention enumerated in paragraphs [0027] and [0035].

The titration analysis system of the invention comprises: (1) an analysis cell; (2) a sampling device for adding a predetermined volume of a sample of the electroless plating bath to the analysis cell; (3) a solution stirring device for stirring the sample; (4) a temperature control device for maintaining the sample at a predetermined temperature; (5) a hydrogen detector, including a hydrogen sensor, for detecting the concentration of hydrogen in the gas phase above the sample; (6) a titrant solution comprising a predetermined concentration of ions of a catalytic metal that catalyzes deposition of the deposited metal; and (7) a titrator device for adding an aliquot of a known volume of the titrant solution to the sample. Optionally, The titration analysis system of the invention may further comprise: (8) a cell cleaning device for cleaning the analysis cell (to remove metal deposits and minimize cross-contamination between analyses).

The sampling device and the titrator device may comprise any suitable solution metering device, including a metering pump or syringe. A wide variety of such devices are available commercially.

The analysis cell may be open at the top or may comprise shielding, a loose fitting lid, for example, to inhibit dispersion of gas from the analysis cell into the ambient atmosphere so as to increase sensitivity to hydrogen generated in the sample at the titration endpoint. The analysis cell may comprise any material compatible with the bath sample. Suitable analysis cell materials include glass and plastic materials, and metals, such as aluminum or stainless steel, for example. Aluminum is particularly suitable as an analysis cell material for the present invention, which involves hydrogen detection as the titration endpoint, since electroless nickel does not readily deposit on oxidized aluminum surfaces, so that cleaning of an aluminum analysis cell is facilitated.

The hydrogen detector generally comprises an electronic module coupled with a hydrogen sensor, which is typically contained in a hydrogen probe. A variety of suitable hydrogen detectors are available commercially. The hydrogen probe, which typically comprises a cylindrical section that includes the hydrogen sensor, is preferably located and configured so that hydrogen gas evolved from the sample is quickly detected but contact of the hydrogen sensor with the bath sample or a rinse solution (which might damage the sensor) is avoided. This may be accomplished, for example, by utilizing a narrow or tapered analysis cell with a high aspect ratio so that the cross-sectional areas of the analysis cell and the hydrogen probe are substantially comparable. In this case, the hydrogen sensor may be positioned sufficiently far (typically several centimeters) from the surface of the bath sample to be out of range of liquid spray and splashes without a substantial reduction in hydrogen sensitivity due to increased sampled gas volume.

Alternatively, appropriate shielding may be provided so that the hydrogen sensor may be placed close to the sample surface without being damaged by spray or splashes of the sample liquid, a cleaning solution, or rinse water. Such shielding may be of any suitable geometric shape and comprise any material compatible with the bath sample, and may be internal or external to the hydrogen probe. Suitable external shielding may be provided by a bent tube of a glass or plastic material, for example.

The temperature of the bath sample may be controlled by any suitable means. In a preferred embodiment, a heat exchange liquid is circulated from a circulator-controller through a jacket on the analysis cell. In another preferred embodiment, an electrical resistance heater is used in conjunction with an electronic temperature controller that includes a temperature sensor. Such temperature controllers are available commercially. The electrical resistance heater may comprise an immersion heater (immersed in the bath sample) or an external heater, a metallic block in contact with the bottom/and or sides of the analysis cell, or electrical heating tape wrapped around the analysis cell, for example. Immersion heaters comprising suitably inert materials, glass or stainless steel, for example, are commercially available. Suitable temperature sensors include thermocouples and thermistors, for example. Alternatively, a hot plate with a temperature sensor could be used. The temperature of the bath sample is preferably controlled within $\pm 1°$ C. or less.

Stirring is needed to mix the bath sample after titrant additions, and also facilitates control of the bath sample temperature. Stirring of the bath sample may be provided any suitable stirring method, including magnetic stirring, mechanical stirring, gas bubbling, liquid circulation and ultrasonic stirring.

The solution stirring device of the apparatus of the invention may be of any suitable type, including a magnetic stirrer, a mechanical stirrer (impellor driven by an electrical motor, for example), a gas bubbler, an ultrasonic wave generator, and a liquid circulator, for example.

Preferably, the analysis cell is cleaned between titrations to avoid cross-contamination of bath samples and to remove metal deposits from the cell walls. An optional cell cleaning device preferably rinses the cell with a cleaning solution, which is pumped or sprayed into the cell and is typically collected for subsequent disposal. A preferred cleaning solution comprises aqua regia or nitric acid, for example, but any suitable cleaning solution may be used. After being cleaned, the cell may also be rinsed with deionized water and/or blow dried to further reduce cross-contamination between the analyses of the invention.

The computing system of the apparatus of the invention comprises: (9) a computing device having a memory element with a stored algorithm operative to effect at least the basic steps of the method of the invention; and (10) an interface enabling the computing device to control the other elements of the apparatus so as to perform at least the basic steps of the method of the invention.

The computing device may comprise a computer with integrated components, or may comprise separate components, a microprocessor and a memory device that includes a memory element, for example. The memory element may be any one or a combination of available memory elements, including a computer hard drive, a microprocessor chip, a read-only memory (ROM) chip, a programmable read-only memory (PROM) chip, a magnetic storage device, a computer disk (CD) and a digital video disk (DVD), for example. The memory element may be an integral part of the computing device or may be a separate device. The interface may be an integral part of the computing device or may be a separate device.

Suitable hydrogen detectors, titrator devices, solution stirring devices, cell cleaning devices, computing devices, memory elements, and interfaces for use in the apparatus of the invention are well known to those skilled in the art.

The basic steps of the method of the invention performed by the device of the invention comprise (a) placing a predetermined volume of the sample in the analysis cell, (b) stirring the sample, (c) maintaining the sample at a predetermined temperature, (d) performing a titration by repeatedly adding an aliquot of a known volume of the titrant solution to the sample and monitoring the concentration of hydrogen in the gas phase above the sample, (e) determining a titration endpoint corresponding to a substantial increase in the concentration of hydrogen in the gas phase above the sample, and (f) calculating the total quantity of the catalytic metal added to the sample at the titration endpoint.

Description of a Preferred Embodiment

FIG. 1 is a schematic representation of a preferred apparatus 100 of the invention, which comprises a computer system 110 and a titrator analysis system 120. Computer system 110 includes an interface 112 enabling computing device 111 to control titrator analysis system 120 and acquire titration analysis data from titrator analysis system 120. The arrows indicate the direction of flow of electrical control signals, acquired data, and the various solutions. Computing device 111 has a memory element 113 with a stored algorithm for effecting at least the basic steps of the analysis of the invention. Computing device 111 may comprise a computer with integrated components, or may comprise separate components, a microprocessor and a memory device that includes memory element 113, for example. Memory element 113 may be an integral part of computing device 111 or may be a separate device. Interface 112 may be an integral part of computing device 111 or may be a separate device.

For the preferred apparatus 100 of FIG. 1, titration analysis system 120 comprises an analysis cell 121 containing a sample 122 of the electroless plating bath, a sampling device 123 for adding a predetermined volume of sample 122 to analysis cell 121, a hydrogen detector system 125 for measuring the concentration of hydrogen in the gas phase above sample 122, a titrator device 124 for adding an aliquot of a known volume of a titrant solution to sample 122, a means for stirring sample 122, a means for controlling the temperature of sample 122, and optionally a means for cleaning analysis cell 121 to minimize cross-contamination between analyses. Analysis cell 121 may be open at the top (as depicted) or may comprise shielding to inhibit dispersion of gas from the analysis cell into the ambient atmosphere. Analysis cell 121 may comprise any material compatible with sample 122, a glass or plastic material, or a metal, such as aluminum or stainless steel, for example. Sampling device 123 and titrator device 124 may comprise any suitable solution metering device, a metering syringe or a metering pump, for example. A wide variety of such devices are available commercially.

For the preferred apparatus of FIG. 1, hydrogen detector system 125 comprises a hydrogen detector 126 coupled with hydrogen probe 127 containing a hydrogen sensor. A variety of suitable hydrogen detector systems are available commercially. In one preferred embodiment, hydrogen probe 127 is preferably shielded, via a bent tube 128, for example, to prevent sample 122, cleaning solution or rinse water from contacting the hydrogen sensor contained in hydrogen probe 127. Bent tube 128, or another type of shield, may comprise any material compatible with sample 122, a glass or a plastic material, for example. In an alternative preferred embodiment (not depicted), the diameter of at least the top section of analysis cell 121 is not substantially larger than the diameter of hydrogen probe 127, and the end of hydrogen probe 127 is positioned sufficiently far from the surface of the bath sample to be out of range of liquid splashes and spray.

For the preferred apparatus of FIG. 1, the temperature of sample 122 is controlled by a temperature controller 130, which includes a temperature sensor (not shown), used in conjunction with a heater element 131 that envelopes at least part of analysis cell 121, the bottom, sides, or both (as depicted), for example. Heater element 131 may comprise an analysis cell jacket through which a heat exchange liquid is circulated from a standard circulator-controller 130 of the type commercially available, for example. Alternatively, heater element 131 may comprise electrical heater tape wrapped around at least part of analysis cell 121 and used in conjunction with a standard temperature controller and a thermocouple or thermistor sensor, placed in contact with analysis cell 121 or sample 122.

For the preferred apparatus of FIG. 1, solution stirring is provided by a magnetic stirrer 140 coupled with a magnetic stir bar 141, but may be provided by any other suitable solution stirring device.

For the preferred apparatus of FIG. 1, optional cell cleaning device 150 rinses analysis cell 121 with a cleaning solution (pumped or sprayed into the cell), which is collected for subsequent disposal. After being cleaned, analysis cell 121 is preferably rinsed with deionized water and/or blow dried to further reduce cross-contamination between the analyses of the invention.

The efficacy of the invention for determining the stability of an electroless plating bath was demonstrated for a commercial electroless nickel bath (Everon B P, Rohm and Haas) comprising 20% Replenisher I solution, 15% Make-up solution, and 65% deionized water (pH 4.9). The analysis cell was a glass test tube, which had a neck of reduced diameter and a volume of 50 mL, and contained a 20-mL sample of the electroless plating bath. The hydrogen probe had an outside diameter of 12 mm and the end of the probe was positioned 11 cm from the bath sample surface. The inside diameter of the analysis cell was 20 mm at the solution level and 15 mm at the probe level. The palladium ion titrant solution contained 23 ppm palladium chloride ($PdCl_2$) and 100 g/L hydrochloric acid. Titrations were performed using a prototype titration analyzer (ECI Technology). During the titration, the solution was stirred via a magnetic stirrer and the sample temperature was maintained at 83° C.±0.3° C. via a standard temperature controller and electrical heating tape wrapped around the sides of the analysis cell. After each addition of the titrant solution, one minute was allowed for solution mixing. Detection of hydrogen at the titration endpoint was provided by a HydroKnowz H2 Detector (Neodym Technologies, Inc., Vancouver, BC, Canada).

Figure 2:
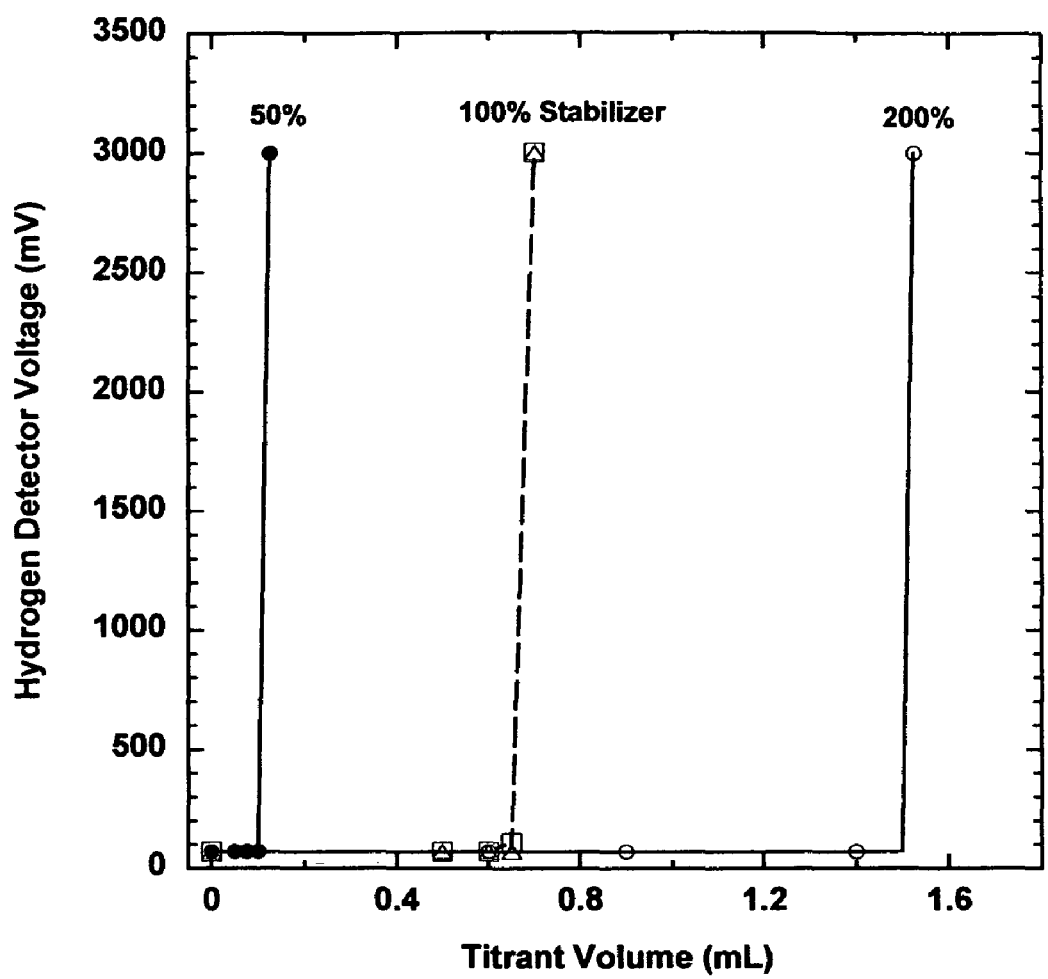
FIG. 2 shows titration curves of the hydrogen detector output voltage as a function of the volume of palladium chloride titrant (23 ppm) added to 20-milliter samples of a commercial electroless nickel plating bath (Everon B P, Rohm and Haas) maintained at 83° C. and containing 50%, 100% (target) or 200% added Stabilizer solution.

FIG. 2 shows titration curves of the voltage output (mV) of the hydrogen detector as a function of the volume of the palladium chloride titrant added to 20-milliter samples of a the Everon B P electroless nickel plating bath (83° C.) containing 50%, 100% (normal target value) or 200% added Stabilizer solution. The titration endpoints are evident as sharp increases, practically a step, in the voltage output of the hydrogen detector. Much more of the palladium ion titrant was required to decompose the bath having the higher stabilizer concentrations.

Table 1 gives the titration data for FIG. 2. In all cases, the voltage output of the hydrogen detector remained constant at 72 mV (corresponding to the hydrogen background noise level) until the titration endpoint, and then practically stepped to 3000 mV (corresponding to saturation of the hydrogen sensor).

TABLE 1

Titration Data for Electroless Nickel Baths with Various Stabilizer Concentrations

| Titrant Volume (mL) | Hydrogen Detector Output (mV) | | | |
|---|---|---|---|---|
| | 50% Stabilizer | 100% Stabilizer | 100% Stabilizer | 200% Stabilizer |
| 0.000 | 72 | 72 | 72 | 72 |
| 0.050 | 72 | | | |
| 0.075 | 72 | | | |
| 0.100 | 72 | | | |
| 0.125 | 3000 | | | |
| 0.500 | | 72 | 72 | 72 |
| 0.600 | | 72 | 72 | 72 |
| 0.650 | | 110 | 72 | |
| 0.700 | | 3000 | 3000 | |
| 0.750 | | | | 72 |
| 0.900 | | | | 72 |
| 1.150 | | | | 72 |
| 1.400 | | | | 72 |
| 1.500 | | | | 72 |
| 1.525 | | | | 3000 |

The preferred embodiments of the present invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

We claim:

1. A method for measuring the stability of an electroless plating bath for depositing a deposited metal, comprising the steps of:
    placing a predetermined volume of a sample of the electroless plating bath in an analysis cell;
    stirring the sample;
    maintaining the sample at a predetermined temperature;
    providing a titrant solution comprising a predetermined concentration of ions of a catalytic metal that catalyzes deposition of the deposited metal;
    performing a titration by repeatedly adding an aliquot of a known volume of the titrant solution to the sample and monitoring the concentration of hydrogen in the gas phase above the sample;
    determining a titration endpoint corresponding to a substantial increase in the concentration of hydrogen in the gas phase above the sample; and
    calculating the total quantity of the catalytic metal added to the sample at the titration endpoint, which provides a measure of the stability of the electroless plating bath.

2. The method of claim 1, wherein the deposited metal is selected from the group consisting of nickel, cobalt, copper, tungsten, molybdenum, rhenium, and combinations thereof.

3. The method of claim 1, wherein the titrant solution comprises palladium compound selected from the group consisting of chloride, sulfate, acetate and combination thereof.

4. The method of claim 1, wherein the titrant solution comprises from 0.05 to 5 mM palladium chloride and from 10 to 200 g/L hydrochloric acid.

5. The method of claim 1, wherein the sample is stirred by a method selected from the group consisting of magnetic stirring, mechanical stirring, gas bubbling, liquid circulation and ultrasonic stirring.

6. The method of claim 1, wherein the predetermined temperature is maintained constant within ±1° C. or less.

7. An apparatus for measuring the stability of an electroless plating bath for depositing a deposited metal, comprising:
    an analysis cell;
    a sampling device for adding a predetermined volume of a sample of the electroless plating bath to the analysis cell;
    a solution stirring device for stirring the sample;
    a temperature control device for maintaining the sample at a predetermined temperature;
    a hydrogen detector, comprising a hydrogen sensor, for detecting the concentration of hydrogen in the gas phase above the sample;
    a titrant solution comprising a predetermined concentration of ions of a catalytic metal that catalyzes deposition of the deposited metal;
    a titrator device for adding an aliquot of a known volume of the titrant solution to the sample;
    a computing device having a memory element with a stored algorithm operative to effect at least the basic steps of the method of the invention, comprising,
        placing a predetermined volume of the sample in the analysis cell, stirring the sample,
        maintaining the sample at a predetermined temperature,
        performing a titration by repeatedly adding an aliquot of a known volume of the titrant solution to the sample and monitoring the concentration of hydrogen in the gas phase above the sample, determining a titration endpoint corresponding to a substantial increase in the concentration of hydrogen in the gas phase above the sample, and calculating the total quantity of the catalytic metal added to the sample at the titration endpoint; and an interface enabling the computing device to control the other elements of the apparatus so as to perform at least said basic steps of the method of the invention.

8. The apparatus of claim 7, wherein the solution stirring device is selected from the group consisting of magnetic stirrer, mechanical stirrer, gas bubbler, ultrasonic wave generator, and liquid circulator.

9. The apparatus of claim 7, further comprising:
a cell cleaning device for cleaning the analysis cell.

10. The apparatus of claim 7, wherein the analysis cell is shielded from the ambient atmosphere.

11. The apparatus of claim 7, wherein the hydrogen detector comprises a hydrogen sensor that is shielded from splashes and spray of a liquid.

12. The apparatus of claim 7, wherein the memory element is selected from the group consisting of computer hard drive, microprocessor chip, read-only memory (ROM) chip, programmable read-only memory (PROM) chip, magnetic storage device, computer disk (CD), digital video disk (DVD), and combinations thereof.

* * * * *